(12) United States Patent
Biswas et al.

(10) Patent No.: US 11,576,623 B2
(45) Date of Patent: Feb. 14, 2023

(54) METHOD FOR GENERATING A MODEL FOR GENERATING A SYNTHETIC ECG AND A METHOD AND SYSTEM FOR ANALYSIS OF HEART ACTIVITY

(71) Applicants: IMEC VZW, Leuven (BE); STICHTING IMEC NEDERLAND, AE Eindhoven (NL); REGENTS OF THE UNIVERSITY OF MINNESOTA

(72) Inventors: Dwaipayan Biswas, Leuven (BE); Luke Everson, Leuven (BE); Mario Konijnenburg, Leuven (BE); Christiaan Van Hoof, Leuven (BE); Nick Van Helleputte, Leuven (BE)

(73) Assignees: IMEC VZW, Leuven (BE); STICHTING IMEC NEDERLAND, Eindhoven (NI); REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 519 days.

(21) Appl. No.: 16/716,991

(22) Filed: Dec. 17, 2019

(65) Prior Publication Data
US 2020/0196897 A1    Jun. 25, 2020

(30) Foreign Application Priority Data
Dec. 20, 2018  (EP) .................................... 18214736

(51) Int. Cl.
| | | |
|---|---|---|
| *A61B 5/024* | (2006.01) | |
| *A61B 5/327* | (2021.01) | |
| *G06N 3/04* | (2006.01) | |
| *G06N 3/08* | (2006.01) | |
| *A61B 5/00* | (2006.01) | |

(52) U.S. Cl.
CPC ........ *A61B 5/7278* (2013.01); *A61B 5/02416* (2013.01); *A61B 5/02438* (2013.01);
(Continued)

(58) Field of Classification Search
None
See application file for complete search history.

(56) References Cited

U.S. PATENT DOCUMENTS

2010/0256511 A1   10/2010  Poree et al.
2015/0031965 A1*   1/2015  Visvanathan ........ A61B 5/0205
                                                  600/323
(Continued)

FOREIGN PATENT DOCUMENTS

EP          3804618 A1 *  4/2021
WO    WO-2018/162957 A1   9/2018

OTHER PUBLICATIONS

Hagan et al., "Training Feedforward Networks with the Marquardt Algorithm" IEEE Transactions on Neural Networks, vol. 5, No. 6, Nov. 1994 (Year: 1994).*
(Continued)

*Primary Examiner* — Colin T. Sakamoto
(74) *Attorney, Agent, or Firm* — Moser Taboada (57) ABSTRACT

A method of generating a model for generating a synthetic electrocardiography (ECG) signal comprises: receiving subject-specific training data for machine learning, said training data comprising a photoplethysmography (PPG) signal acquired from the subject and an ECG signal acquired from the subject, wherein the ECG signal provides a ground truth of the subject for associating the ECG signal with the PPG signal; using associated pairs of a time-series of the PPG signal and a corresponding time-series of the ECG signal as input to a deep neural network, DNN; and determining, through the DNN, a subject-specific model relating the PPG signal of the subject to the ECG signal of the subject for converting the PPG signal to a synthetic ECG signal using the subject-specific model.

18 Claims, 5 Drawing Sheets

(52) U.S. Cl.
CPC .............. *A61B 5/681* (2013.01); *A61B 5/327* (2021.01); *A61B 5/7207* (2013.01); *A61B 5/7267* (2013.01); *G06N 3/0454* (2013.01); *G06N 3/08* (2013.01)

(56) References Cited

U.S. PATENT DOCUMENTS

| | | | | |
|---|---|---|---|---|
| 2015/0164404 | A1* | 6/2015 | Euliano | G16H 40/63 600/301 |
| 2017/0209053 | A1* | 7/2017 | Pantelopoulos | A61B 5/7264 |
| 2018/0085020 | A1* | 3/2018 | Segman | A61B 5/327 |
| 2019/0021615 | A1* | 1/2019 | Rundo | G16H 10/60 |
| 2019/0117096 | A1* | 4/2019 | Rundo | A61B 5/02405 |
| 2019/0159735 | A1* | 5/2019 | Rundo | A61B 5/0261 |
| 2019/0298272 | A1* | 10/2019 | Persen | A61B 5/02405 |
| 2020/0015755 | A1* | 1/2020 | Zhao | G16H 50/20 |
| 2020/0100693 | A1* | 4/2020 | Velo | A61B 5/746 |

OTHER PUBLICATIONS

IBM Cloud Education, "What are Neural Networks", Neural Networks, IBM Cloud Learn Hub, Aug. 17, 2020, accessed Jun. 7, 2022 (Year: 2020).*

Banerjee et al., "Estimation of ECG parameters using photoplethysmography", 13th IEEE International Conference on Bioinformatics and Bioengineering, Nov. 10, 2013, pp. 1-5.

Zhang et al.,: "TROIKA: A General Framework for Heart Rate Monitoring Using Wrist-Type Photoplethysmographic Signals During Intensive Physical Exercise", IEEE Transaction on Biomedical Engineering, vol. 62, No. 2, pp. 522-531, Feb. 2015.

Shashikumar et al., "A Deep Learning Approach to Monitoring and Detecting Atrial Fibrillation using Wearable Technology", 2017 IEEE EMBS International Conference on Biomedical & Health Informatics, Orlando, FL, USA, Feb. 16-19, 2017, pp. 141-144.

Coco et al., "PPG Sensors for Detection of Car Driver Drowsiness", Poster at 68th SIF National Congress Italian Physiological Society, Pavia, Italy, Sep. 6-8, 2017.

Cicone et al., "How Nonlinear-Type Time-Frequency Analysis Can Help in Sensing Instantaneous Heart Rate and Instantaneous Respiratory Rate from Photoplethysmography in a Reliable Way", Frontiers in Physiology, vol. 8. Article 701,Sep. 22, 2017.

Raluca Maria et al., "MIoT Applications for Wearable Technologies Used for Health Monitoring", 2018 10th International Conference on Electronics, Computers and Artificial Intelligence, Jun. 28, 2018, pp. 1-4.

Extended European Search Report for Application No. EP18214736.3 dated Jun. 26, 2019.

* cited by examiner

METHOD FOR GENERATING A MODEL FOR GENERATING A SYNTHETIC ECG AND A METHOD AND SYSTEM FOR ANALYSIS OF HEART ACTIVITY

CROSS-REFERENCE TO RELATED APPLICATION

The present application is based on priority claimed on European Patent Application No. 18214736.3, filed on Dec. 20, 2018, the contents of which are incorporated herein by reference.

TECHNICAL FIELD

The present inventive concept relates to a method and a system for analysis of heart activity. In particular, the present inventive concept relates to generating a model which may be used to determine heart activity based on a photoplethysmography (PPG) signal.

BACKGROUND ART

Acquisition of signals representing a heart activity of a subject is important or of interest in many contexts. Heart rate estimation may be of particular interest. The estimated heart rate may be used in clinical settings to provide information for treatment of the subject, but may also be used for general monitoring of a physical condition of the subject. Also, monitoring of heart activity may be of interest to the subject, e.g. for monitoring exercise or other activities of the subject.

Photoplethysmography (PPG) is a technology of interest in monitoring heart activity as it may be provided in a wearable device which may minimally affect a comfort of the subject wearing the device. For instance, a PPG signal may be acquired from peripheral positions on the subject, such as earlobes, fingertips or wrist. Thus, using sensor for acquiring a PPG signal may be advantageous over sensors acquiring an electrocardiography (ECG) signal, as ECG sensor may require placement of ground and reference sensors proximal to the chest of the subject. PPG sensors may provide a small form factor and may be embedded into a wearable device, which may provide heart rate estimation for unobtrusive daily usage. In particular, the PPG sensor may be embedded into a wristband.

However, the PPG signal may be affected by motion artifacts. Thus, if the subject is moving, motion artifacts may be generated which may cause quality of an acquired PPG signal to deteriorate or may prevent making any assessments based on the PPG signal. This is accentuated, when the PPG signal is acquired during daily life of a subject. For instance, motion artifacts may be caused by physical activity of the subject, by ambient light leaking through a widening gap between sensor and a skin surface of the subject during motion and a change in blood flow due to movements. The motion artifacts may cause a spectral component of the artifacts to overpower a heart-beat related PPG component, such that the motion artifact may prevent accurate estimation of the heart rate.

Motion artifacts may be attempted to be removed from the PPG signal. However, removal of motion artifacts may also remove important information from the PPG signal. Alternatively, features of the PPG signal may be extracted to determine the heart rate, but information in the PPG signal may also be lost by such extraction.

Thus, the heart rate estimation from PPG signals may be improved to provide a more robust heart rate estimation.

SUMMARY

An objective of the present inventive concept is to enable improved heart rate estimation from PPG signals in presence of motion artifacts. Another objective of the present inventive concept is to generate a model for heart rate estimation from a PPG signal, such that the PPG signal may be used without need of any additional data to estimate heart rate of a subject.

These and other objectives of the invention are at least partly met by the invention as defined in the independent claims. Preferred embodiments are set out in the dependent claims.

According to a first aspect, there is provided a method of generating a model for generating a synthetic electrocardiography (ECG) signal, said method comprising: receiving subject-specific training data for machine learning, said training data comprising a photoplethysmography (PPG) signal acquired from the subject and an ECG signal acquired from the subject, wherein the ECG signal provides a ground truth of the subject for associating the ECG signal with the PPG signal; using associated pairs of a time-series of the PPG signal and a corresponding time-series of the ECG signal as input to a deep neural network (DNN); and determining, through the DNN, a subject-specific model relating the PPG signal of the subject to the ECG signal of the subject for converting the PPG signal to a synthetic ECG signal using the subject-specific model.

According to the inventive concept, machine learning is used to generate a model for generating a synthetic ECG signal based on a PPG signal. The machine learning may be performed without attempting to extract particular features from the PPG signal. Rather, a complete PPG signal may be used as basis for forming a synthetic ECG signal and information in the PPG signal is not discarded.

It should be realized that the method may comprise extracting, through the DNN, a temporal feature from the time-series of the PPG signal, wherein the temporal feature is representative of heart activity and may be related to the ECG signal. Thus, the DNN may act as a feature extractor which removes the need for feature engineering. The DNN may take raw high dimensional time data as input and transform it into a lower dimensional temporal-feature domain. The determined subject-specific model may be particularly accurate when subject-specific training data is used together with a DNN that does not only generate the model but also takes on the task of feature extraction.

The synthetic ECG signal may be used for extracting features in the synthetic ECG signal so as to provide e.g. metrics on heart activity, such as heart rate or heart rate variability. In particular, the ECG signal may be used for extraction of R-peaks, which may be used for determining heart rate and heart rate variability. Thus, the synthetic ECG signal may be intended to be used in analyzing the heart activity of the subject by further processing the synthetic ECG signal.

However, thanks to the generation of the synthetic ECG signal, the ECG signal may also be presented to a physician who is used to analyzing such signals and may thus enable further conclusions to be drawn based on the acquired PPG signal.

The training data is subject-specific, which implies that the model is created to enable PPG signals of a specific subject to be used for generating synthetic ECG signals.

Thus, the DNN may be taught to provide a model which may enable correct generation of a synthetic ECG signal in relation to typical artifacts of the subject, such as motion artifacts or other variations in the heart signal of the subject. The physiology is different between different subjects which also implies that variations in PPG signals and artifacts occur between different subjects. However, since a subject-specific model is formed, the variation in artifacts may be relatively limited to allow the DNN to correctly generate a model for converting the PPG signals to synthetic ECG signals.

According to an embodiment, said training data comprising a PPG signal from the subject is acquired by a PPG sensor in contact with the subject. Preferably, the PPG sensor is arranged in tight contact, such as by wearing the PPG sensor in a wristband that is worn tightly by the subject. The PPG sensor being in contact with the subject ensures that a well-defined relationship between the PPG sensor and the subject is established so as to reduce influence of motion artifacts on the acquired PPG signal.

In generating the model, an ECG signal is included in the training data. The model is thus formed to relate the PPG signal to ECG signals of the subject. Once the model has been generated and is deployed, forming of a synthetic ECG signal is enabled based on only the PPG signal and there is no need of any other additional signal in order to estimate the ECG signal of the subject.

It should be realized that the DNN need not necessarily generate the subject-specific model from scratch. Rather, a general model for relating a PPG signal to an ECG signal may be stored based on previously determined models. The general model may be associated with certain characteristics of the subject, such as heart condition, age, gender, body mass index, etc. Thus, the DNN may use the general model as input to adapt the general model to the subject-specific training data for forming the subject-specific model.

However, as an alternative, the DNN does not use any predetermined information on relations between PPG signals and ECG signals. Rather, the DNN may form the subject-specific model based merely on the information in the subject-specific training data.

According to an embodiment, the method further comprises associating the determined subject-specific model with the specific subject.

This implies that the model is associated to the specific subject for which the model is generated. Thus, the method is configured to generate a single model for each subject, such as to form a one-to-one relationship between models and subjects.

According to an embodiment, the subject-specific model is configured to convert a first time-series of the PPG signal to a second time-series of the ECG signal, wherein the second time-series is shorter than the first time-series.

The ECG signal may typically contain more detailed information on the heart activity of the subject than the PPG signal. Thus, by using a longer time-series of the PPG signal, the amount of information that may be extracted from the PPG signal may be converted to a shorter time-series of the ECG signal with a corresponding amount of information. For instance, a 2:1 relationship may be used such that the first time-series is two times longer than the second time-series.

It should be realized that the consecutive time-series of the synthetic ECG signal may be based on overlapping time-series of the PPG signal, such that each portion of the synthetic ECG signal over a long period of time is based on a corresponding moment in time of the PPG signal.

According to an embodiment, the time-series of the PPG signal and the corresponding time-series of the ECG signal in an associated pair represent slightly different points in time to take pulse transit time into account.

The PPG signal may be measured e.g. at a wrist of the subject. Thus, there is a difference in time between the ECG signal and the PPG signal, often referred to as pulse transit time (PTT), i.e. a time used for blood flow to travel from the heart to the wrist for being sensed by a PPG sensor.

The associated pairs of time-series of PPG and ECG signals may take the PTT into account. The time relation between the PPG and ECG signals may be automatically identified by relating distinct features in the ECG signal to corresponding distinct features in the PPG signal to identify a time delay of the PPG signal.

The subject-specific model may also incorporate the delay so as to enable forming the synthetic ECG signal to be associated with a correct timing of the ECG signal. This may require that a PPG sensor used for acquiring subject-specific training data is similarly arranged on the subject during a training phase and a deployment phase (when the PPG sensor is used for generating the synthetic ECG signal based on the model).

According to an embodiment, the DNN comprises a stack of neural network layers.

The stack of neural network layers may allow different functions of the DNN to be provided in different neural network layers. The stack may then in combination enable forming of a robust model for generating the synthetic ECG signal.

According to an embodiment, the stack of neural network layers comprises one or more convolutional neural network (CNN) layers, followed by one or more deconvolutional neural network (DCNN) layers.

The CNN layers may be configured to down-sample information in the PPG signal to reduce dimensionality of the PPG signal and enable the model to learn higher-order features of data. Then, DCNN layers are used to again upsample the output from the CNN layers to form an output corresponding to the ECG signal.

The stack of neural network layers may use a hierarchical structure of DCNN layers. This implies that different levels of shape details of the ECG signal may be captured.

According to an embodiment, the received subject-specific training data comprises a set of PPG signals and a set of ECG signals, each set including signals acquired in relation to different activities of the subject.

Thanks to the subject-specific training data being acquired in relation to different activities, the training data may include different types of artifacts and various different shapes of the PPG and ECG signals of the subject. This may ensure that a model may be generated which may provide a more robust generation of a synthetic ECG signal, e.g. for various different levels of the heart rate.

According to an embodiment, said training data further comprises abnormality data corresponding to abnormalities of heart functioning acquired from other subjects, said abnormality data comprising a PPG signal and an associated ECG signal.

It may be desired to use the model for identifying abnormalities of heart function. However, such abnormalities may not occur during a training phase for capturing training data for the machine learning, if the subject during training is healthy. Thus, training data may not include information on abnormalities acquired from the subject. Instead, during a training phase, examples of abnormalities, which may be previously acquired from other subjects, may be included in the training data so as to enable the machine learning to be based also on abnormality data. The model may thus be used to also predict abnormalities in heart function during the deployment phase.

Abnormality data may for instance include examples of heart disease, such as arrhythmia, tachycardia and brachycardia.

According to a second aspect, there is provided a computer program product comprising computer-readable instructions such that when executed on a processing unit the computer-readable instructions will cause the processing unit to perform the method according to the first aspect.

Effects and features of this second aspect are largely analogous to those described above in connection with the first aspect. Embodiments mentioned in relation to the first aspect are largely compatible with the second aspect.

The computer program product may implement the method in a processing unit, which may be a dedicated processing unit for performing the method or may be a general-purpose processing unit which may be able to perform the method based on the computer program product.

The computer program product may comprise a computer readable medium, such as providing computer-readable instructions stored on e.g. a computer memory, a compact disc or a digital versatile disc.

The computer program product may be provided as a software which may be downloaded e.g. from a server, such that the computer program product may be received as a signal carrying the computer-readable instructions.

According to a third aspect, there is provided a method for analysis of heart activity of a subject based on a photoplethysmography (PPG) signal from the subject, said method comprising: acquiring subject-specific training data for machine learning, said training data comprising a PPG signal acquired from the subject and an electrocardiography (ECG) signal acquired from the subject, wherein the ECG signal provides a ground truth of the subject for associating the ECG signal with the PPG signal; transferring the subject-specific training data to a deep neural network (DNN); receiving a subject-specific machine-learned model from the DNN, wherein the model defines a relation of a time-series of the PPG signal of the subject to a corresponding time-series of the ECG signal of the subject; acquiring a PPG signal from the subject for analysis of the heart activity of the subject; and determining a synthetic ECG signal of the subject based on subject-specific model and the acquired PPG signal for analysis of the heart activity of the subject.

Effects and features of this third aspect are largely analogous to those described above in connection with the first and second aspects. Embodiments mentioned in relation to the first and second aspects are largely compatible with the third aspect.

According to the third aspect, a training phase may be used for acquiring subject-specific training data, which is used to generate a model. Then, in a deployment phase, the model may be used so as to enable determining a synthetic ECG signal based on a PPG signal.

The method may use the synthetic ECG signal in order to determine features regarding heart activity from the synthetic ECG signal. For instance, heart rate and/or heart rate variability may be determined based on the synthetic ECG signal and may further be output for presentation to a user. However, thanks to the forming of the synthetic ECG signal, the information acquired by the PPG signal may be converted into a representation which may allow further conclusions to be drawn from the acquired information, so as to e.g. enable a physician to draw conclusions on heart condition from the acquired data.

The forming of the synthetic ECG signal may thus enable more in-depth analysis of heart condition based on an acquired PPG signal.

The synthetic ECG signal may be determined as an intermediate step in processing of the PPG signal. This may allow a user, such as a physician, to request a portion of the synthetic ECG signal to be output, e.g. corresponding to a period of deviations in the heart rate. Thus, rather than continuously outputting the synthetic ECG signal, the ECG signal may be output only in periods of interest.

According to an embodiment, said training data comprising a PPG signal from the subject is acquired by a PPG sensor in contact with the subject. Preferably, the PPG sensor is arranged in tight contact, such as by wearing the PPG sensor in a wristband that is worn tightly by the subject. The PPG sensor being in contact with the subject ensures that a well-defined relationship between the PPG sensor and the subject is established so as to reduce influence of motion artifacts on the acquired PPG signal.

The method according to the third aspect may be performed in a wearable device carrying a PPG sensor. The wearable device may further include an ECG sensor for acquiring an ECG signal or, alternatively, the wearable device may be connected to the ECG sensor during the training phase. For instance, a wireless connection may be established during the training phase, such that the wearable device may collect and package both ECG signals and PPG signals as subject-specific training data. The subject-specific training data may then be transferred to a neural network. The neural network may be provided in a separate, external unit, such that the wearable device may transfer the subject-specific training data to the external unit. For instance, the subject-specific training data may be transferred over a computer network, such as the Internet, so that the neural network may be implemented on an external unit "in the cloud". The wearable device may transfer the subject-specific training data to the computer network through a wired or wireless connection. However, the neural network may be provided in the wearable device itself for generating the model within the wearable device.

It should also be realized that the ECG signals of the subject-specific training data may be separately transferred to the neural network. Thus, the ECG signal and the PPG signal may be acquired by separate devices, which may each communicate acquired data separately to the neural network. For instance, the ECG sensor may, independently from a wearable device carrying the PPG sensor, communicate with an external unit for generating the model. Thus, the external unit may be configured to associate the ECG signal with the PPG signal in order to enable generating of the model. The ECG signal and the PPG signal may be time-stamped using synchronized clocks in order to enable correctly associating the ECG signal with the PPG signal (also taking the pulse transit time into account).

According to an embodiment, the method further comprises extracting R-peaks based on the synthetic ECG signal.

Extraction of R-peaks may allow determining metrics of heart activity. For instance, by extracting R-peaks, intervals between sequential R-peaks may be determined, which may be used for determining instantaneous heart rate. Also, heart rate variability may be determined, i.e. a measure of a difference in the beat-to-beat interval. Such metrics may not conventionally be determined based on a PPG signal, which typically is configured to determine an average heart rate over a period of time.

According to an embodiment, the training data is acquired during an initial training period for generation of the machine-learned model, and after the subject-specific machine-learned model has been generated, the determining of the synthetic ECG signal of the subject based on the PPG signal is enabled.

Thus, training data may first be acquired during a training period. The model may be generated once a sufficient amount of training data has been acquired. Once a model has been generated, the model may be verified, e.g. against a part of the training data or against data acquired in an additional verification period. Thus, a verification may be performed to ensure that the model is able to reliably generate a synthetic ECG signal. Then, when a reliable model has been generated, the model may be deployed to allow generation of the synthetic ECG signal based only on the PPG signal.

According to an embodiment, the method further comprises updating the subject-specific machine-learned model after the subject-specific machine-learned model has been initially generated, said updating comprising during an updating training period: acquiring subject-specific updating training data for machine learning, said updating training data comprising a PPG signal from the subject and an ECG signal from the subject, wherein the ECG signal provides a ground truth of the subject for associating the ECG signal with the PPG signal; transferring the subject-specific updating training data to the DNN; receiving an updated subject-specific machine-learned model from the DNN, wherein the updated model defines a relation of a time-series of the PPG signal of the subject to a corresponding time-series of the ECG signal of the subject.

Physiological factors of a subject may change over time. Thus, additional training data may be needed from time to time to ensure that the model continues to allow correct generation of the synthetic ECG signal from the PPG signal. The updating training period may be periodically triggered to ensure that a reliable model is maintained. Alternatively, a subject may trigger an updating training period when suspecting that an updated model may be needed.

The updating training data may first be used to verify whether any update of the model is needed. Thus, if the model is able to reliably generate the synthetic ECG signal as may be confirmed against the ground truth of ECG signals, a determination that no update is needed may be made. Thus, the initial verification based on the training data may ensure that processing resources are saved, as generation of the updated model is only triggered when necessary.

According to a fourth aspect, there is provided a computer program product comprising computer-readable instructions such that when executed on a processing unit the computer-readable instructions will cause the processing unit to perform the method according to the third aspect.

Effects and features of this fourth aspect are largely analogous to those described above in connection with the first, second and third aspects. Embodiments mentioned in relation to the first, second and third aspects are largely compatible with the fourth aspect.

The computer program product may be provided to a processing unit, which may be arranged in a wearable device comprising the PPG sensor. Thus, the computer program product may be executed to perform the method in a wearable device. However, it should be realized that the computer program product may alternatively be provided to a processing unit which is arranged in an intermediate unit. Thus, the intermediate unit may be configured to acquire PPG signals by receiving the PPG signals from a PPG sensor, which may be arranged in the wearable device, which is physically separate from the intermediate unit.

The computer program product may comprise a computer readable medium, such as providing computer-readable instructions stored on e.g. a computer memory, a compact disc or a digital versatile disc.

The computer program product may be provided as a software which may be downloaded e.g. from a server, such that the computer program product may be received as a signal carrying the computer-readable instructions.

According to a fifth aspect, there is provided a system for analysis of heart activity of a subject based on a photoplethysmography (PPG) signal from the subject, said system comprising: a PPG sensor for acquiring a PPG signal from the subject, a communication unit, which is configured to communicate with a deep neural network (DNN) for machine learning, wherein the communication unit is configured to acquire from the PPG sensor subject-specific training data for machine learning, said training data comprising the PPG signal acquired from the subject; the communication unit being further configured to transfer the subject-specific training data to the DNN, which further receives an electrocardiography (ECG) signal acquired from the subject, wherein the ECG signal provides a ground truth of the subject for associating the ECG signal with the PPG signal, and the communication unit being further configured to receive a subject-specific machine-learned model from the DNN, wherein the model defines a relation of a time-series of the PPG signal of the subject to a corresponding time-series of the ECG signal of the subject; and a processor, which is configured to receive the subject-specific model from the communication unit and, after receiving the subject-specific model, receive the PPG signal from the PPG sensor for analysis of the heart activity of the subject; the processor being further configured to determine a synthetic ECG signal of the subject based on the received subject-specific model and the PPG signal for analysis of the heart activity of the subject.

Effects and features of this fifth aspect are largely analogous to those described above in connection with the first, second, third and fourth aspects. Embodiments mentioned in relation to the first, second, third and fourth aspects are largely compatible with the fifth aspect.

The system may be configured to acquire a PPG signal during a training period such that a subject-specific model may be generated and, once the model has been generated, the system may be able to generate synthetic ECG signals based merely on the PPG signal.

The system may be able to store a plurality of models for different subjects, such that the system may be shared by different subjects and enables generating of synthetic ECG signals based on separately trained models. In this regard, the system may enable a subject to input identity information so as to activate the relevant model. Alternatively, the system may automatically identify the subject among the subjects for which models are stored in the device, e.g. based on subject-specific characteristics of the PPG signal.

According to an embodiment, the PPG sensor may be configured to be arranged in contact with the subject for detecting the PPG signal of the subject. The PPG sensor being in contact with the subject ensures that a well-defined relationship between the PPG sensor and the subject is established so as to reduce influence of motion artifacts on the acquired PPG signal.

According to an embodiment, the system further comprises an ECG sensor, such that the system may acquire the ECG signal during the training period. Once the model has been generated, the ECG sensor may be de-activated, e.g. for saving power, and the PPG signal may still be used to generate the synthetic ECG signal.

According to another embodiment, the system further comprises a receiver, configured to be connected to an ECG sensor for acquiring an ECG signal from the subject. For instance, the receiver may form a wired or wireless connection to the ECG sensor for receiving the ECG signal. Thus, the system may collect subject-specific training data including PPG signals and ECG signals, without the device including an ECG sensor.

The communication unit may thus be configured to acquire the training data from the PPG sensor and the receiver. The communication unit may then further transfer the subject-specific data comprising the PPG signal and the ECG signal to the neural network.

According to yet another embodiment, the communication unit of the device only transfers the acquired PPG signal from the subject to the neural network. The ECG sensor may then be external to the system and may be configured to separately communicate the ECG signal to the neural network.

According to an embodiment, the system further comprises a carrier, which is configured to be worn by the subject, wherein the PPG sensor, the communication unit and the processor are arranged in or on the carrier.

Thus, the system may be arranged in a single physical unit and may be implemented in a wearable carrier.

Thus, the system may be conveniently worn by the subject, so as to allow generating a synthetic ECG signal in an unobtrusive manner, not affecting daily life of the subject.

The carrier may be configured to be worn on a wrist of a subject. This may be particularly convenient to the subject. For instance, the system may be embedded into a smart watch, which may be worn on the wrist.

It should be realized that the device may comprise a carrier which may be worn in another manner on the subject. For instance, the carrier may alternatively be configured to be worn on an earlobe or a fingertip of the subject.

According to an embodiment, the receiver, configured to be connected to an ECG sensor for acquiring an ECG signal from the subject, may further be arranged in or on the carrier.

However, it should be realized that according to alternatives, the system may be distributed in a plurality of physical units. For instance, the PPG sensor may be arranged in or on the carrier, whereas the communication unit and the processor may be arranged in one or more separate physical units, which may or may not be worn by the subject, and may be configured to communicate with the PPG sensor for receiving PPG signals.

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

DETAILED DESCRIPTION OF THE INVENTION

The inventive concept enables generating a synthetic electrocardiography (ECG) signal from a photoplethysmography (PPG) signal. A machine-learned model is generated for relating the PPG signal to ECG signals, such that, once generated, generation of a synthetic ECG signal is enabled using only the PPG signal.

The machine-learned model may be generated in a supervised framework, wherein an ECG signal providing a ground truth is included for assisting generation of the model. During a dedicated training phase, a relationship between time intervals of the PPG signal (in time windows or frames) and the corresponding ECG signal (considered as ground truth) are learnt. Once trained, the model may predict the ECG signal for a test set of PPG data. The predictions may be verified against the ground truth ECG signal to verify that the model is effective in predicting ECG signals from PPG signals.

The predictions may be verified by extracting R-peaks from the synthetic ECG signal, e.g. using Pan Tompkins's algorithm, and verifying the extracted R-peaks against R-peaks extracted from the ground truth ECG signal.

After verification of the model, the model may be used in a deployment phase, wherein PPG signals may be acquired and synthetic ECG signals may be predicted based on the PPG signals and the generated model, without a need to acquire any ECG signals in the deployment phase.

It should be realized that other signals or information may be acquired in association with the PPG signal, but are not necessary in order to enable generation of a synthetic ECG signal.

The machine learning framework may be used in a personalized use-case scenario. The basic premise of this use-case rests on the fact that biological signals are influenced by various physiological factors—age, sex, height, weight/body-mass-index, etc. and most importantly the cardiac condition of a given subject. Thus, a neural network may be trained to build a model which learns the underlying subject-specific data distribution.

For better generalization, the model could learn possible variations inherent within the data. Hence, the model may be cross-validated over a training dataset and prospectively evaluated on test data.

Thanks to the generation of a subject-specific model, manual extraction of features in the PPG signal may not be needed in order to enable a reliable model for analysis of heart activity to be formed based on the PPG signal. Also, extensive processing of the PPG signal to reduce or remove motion artifacts or other noise may not be needed to be performed before training of the model. Thus, the input for training may include all information available in the PPG signal so as to allow the model to consider the entire PPG signal in the generation of the model. This may allow a robust and reliable model to be generated.

Figure 1:
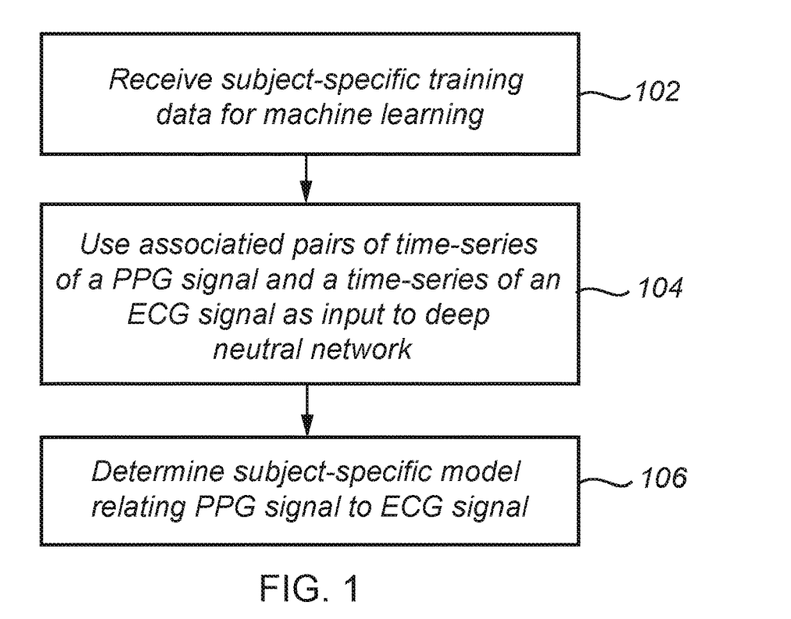
FIG. 1 is a flow chart illustrating a method for generating a subject-specific model for generating a synthetic ECG signal according to an embodiment.

Referring now to FIG. 1, a method of generating the model for generating synthetic ECG signals will be generally described.

The method comprises receiving, step 102, subject-specific training data for machine learning. The subject-specific training data may be received by any processing unit which may be configured to perform machine learning. The processing unit may comprise extensive computing power in order to enable performing of the machine learning. For instance, the processing unit may be implemented as any computer unit (or network of computer units) which may be connected to a communication network for receiving the training data. Thus, the processing unit may be implemented "in the cloud". The processing unit may be configured to receive the training data from sensor(s) used for acquiring the training data. The communication of the training data may take place via a number of intermediate nodes, such that the training data may e.g. be provided via the Internet.

The training data may comprise a PPG signal acquired from the subject and an ECG signal acquired from the subject, wherein the ECG signal provides a ground truth for associating the ECG signal with the PPG signal.

The method further comprises using, step 104, associated pairs of a time-series of a PPG signal and a corresponding time-series of the ECG signal as input to a deep neural network (DNN).

The time-series of the PPG signal may be slightly shifted in time in relation to the time-series of the ECG signal. This is due to the PPG signal being acquired e.g. at a wrist of the subject and hence experiencing a delay corresponding to the time required for blood flow to travel from the heart to the wrist, which may be referred to as pulse transit time (PTT).

The time shift due to PTT may be automatically detected by means of relating features in the PPG signal to corresponding features in the ECG signal. However, according to an alternative, the PTT time shift may be manually determined and provided as input to the DNN.

The DNN may be implemented in the processing unit described above. Thus, the DNN may receive ECG signals that are related to the PPG signals in the corresponding time frames for training the DNN to generate a model.

The PPG signal may be provided as a raw signal, which may possibly have been pre-processed. The information relating to heart activity in the PPG signal may be maintained, such that a complete dataset of the time-series of the acquired PPG signal is used for training the model. For instance, the PPG signal need not be subject to extracting features or removing periods of the PPG signal in which motion artifacts are present. Rather, the entire PPG signal may be used for enabling the neural network to be taught to handle artifacts within the PPG signal and still provide a synthetic ECG signal. The PPG signal may thus form a signal which is continuous in time by including periodical samples in the time-series.

The method further comprises determining, through the DNN, step 106, a subject-specific model relating the PPG signal of the subject to the ECG signal of the subject. The determination of the subject-specific model may thus utilize complete datasets of the PPG signal to generate a reliable model for enabling converting PPG signals of the subject to synthetic ECG signals of the subject.

The training data provided to the DNN may further comprise abnormality data corresponding to abnormalities of heart functioning acquired from other subjects. Such training data may be used when the machine-learned model is to be used e.g. in disease prediction scenario. Then, training data for a healthy subject may be complemented by abnormality data to enable the model to be taught to predict and identify abnormal heart condition.

The abnormality data used may thus be based on at least one other subject, which exhibits the abnormalities of heart function of interest. The abnormality data may comprise a PPG signal acquired from the at least one other subject and an ECG signal acquired from the same at least one other subject, wherein the ECG signal provides a ground truth for associating the ECG signal with the PPG signal in an abnormal heart condition.

The abnormality data may comprise examples from a plurality of other subjects, which may ensure that the prediction of the abnormal heart condition in the healthy subject is not closely linked to specific shapes of the PPG and ECG signals in an abnormal heart condition for a single other subject.

The abnormality data may for instance include examples of heart disease, such as arrhythmia, tachycardia and brachycardia. Thus, the model may then enable generating a synthetic ECG signal in case of the subject, being healthy during the training phase, experiencing e.g. arrhythmia in the deployment phase.

Figure 2:
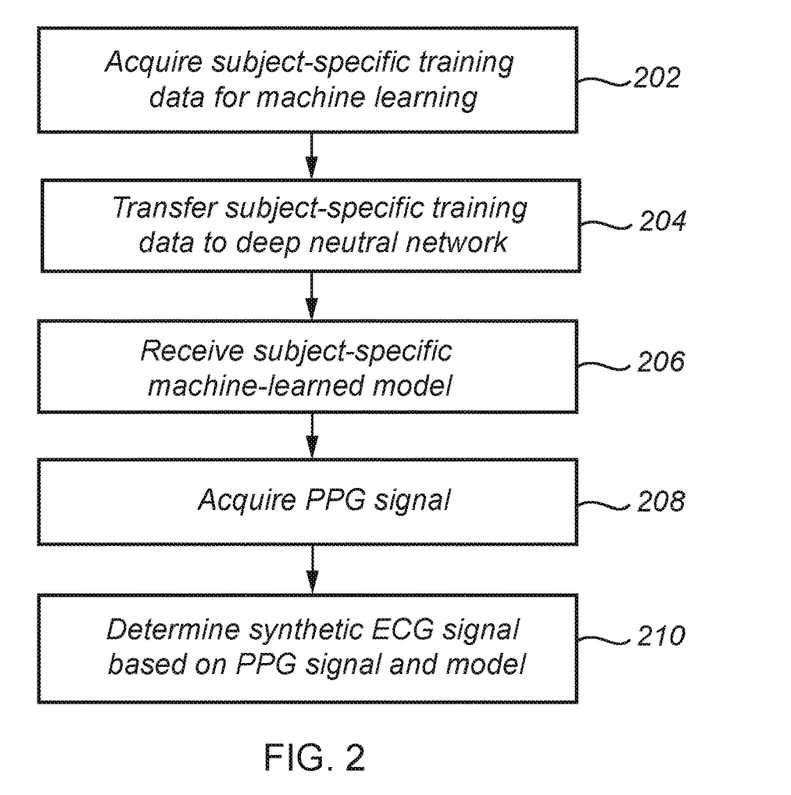
FIG. 2 is a flow chart illustrating a method for acquiring data for generating the model and for using the generated model according to an embodiment.

Referring now to FIG. 2, a method of using the model will be described. Since a subject-specific model is generated, training data may first need to be acquired from the subject and then the generated model may be deployed for use for the subject. This implies that the same device may be used for acquiring training data and may later receive the model for enabling converting a PPG signal to a synthetic ECG signal.

Thus, the method may comprise acquiring, step 202, subject-specific training data for machine learning. The training data comprises a PPG signal from the subject and an ECG signal from the subject, wherein the ECG signal provides a ground truth of the subject for associating the ECG signal with the PPG signal.

The acquiring of subject-specific training data may be controlled by a device which comprises a PPG sensor, such as a wearable device, e.g. a wristband. The device may acquire the PPG signal through the PPG sensor. Further, the device may acquire the ECG signal by receiving the ECG signal from an ECG sensor, which may be arranged in a different physical unit. Thus, the ECG sensor may be configured to communicate with the device comprising the PPG sensor for transferring detected ECG signals to the device through wired or wireless communication.

As an alternative, the acquiring of subject-specific training data may be controlled by a central unit. The central unit may acquire the PPG signal and the ECG signal by receiving the PPG signal from a PPG sensor and the ECG signal from an ECG sensor. The PPG sensor, the ECG sensor and the central unit may each be arranged in different physical units, and may be configured for wired or wireless communication for transferring PPG signals and ECG signals to the central unit. For instance, the central unit may be configured as a mobile phone, which may communicate with the PPG sensor and the ECG signal.

The method may further comprise transferring, step 204, the subject-specific training data to a DNN, which may be configured to perform machine learning for generating a machine-learned model.

The DNN may be implemented in a computer unit, which may be remote from the PPG sensor and the ECG sensor. The DNN may be configured to receive subject-specific training data relating to different subjects, such that the same DNN may perform machine learning for different subjects spread out across the world. Thus, the subject-specific training data may be transferred through a computer and/or telecommunication network in order to reach the DNN. However, it should also be realized that the DNN may be implemented by a subject receiving a software executing the DNN for installation on a computer unit, such as a personal computer or a mobile phone, owned by the subject. Thus, the transferring of the subject-specific training data may comprise communicating the subject-specific training data over a direct communication link between the PPG sensor and the ECG sensor and the computer unit on which the DNN is installed. As yet another alternative, the DNN may even be installed in a device carrying the PPG sensor and/or the ECG sensor, such that the transfer of the subject-specific training data to the DNN may comprise transfer of data between processes in the device.

The PPG signals and the ECG signals may be formed into one or more combined packages for transferring the PPG signals and the ECG signals together to the DNN. However, as an alternative, the PPG signals and the ECG signals may be separately transferred, such that the transfer of the subject-specific data comprises transferring the PPG signal and transferring the ECG signal. The PPG signal may be transferred by a communication unit associated with the PPG sensor, whereas the ECG signal may be transferred by a communication unit associated with an ECG sensor. Thus, the PPG signals and the ECG signals may be separately received by a DNN, which may associate the signals therein for performing the machine learning.

The method further comprises receiving, step 206, a subject-specific machine-learned model from the DNN. Thus, the model may be provided to a processor in which the generation of synthetic ECG signals is to be performed based on the PPG signal. For instance, the processor may be arranged in a device carrying the PPG sensor or in another device which is worn by the subject or in vicinity of the subject, such as an equipment in a hospital in which the subject is being treated.

Thus, the method may further comprise acquiring, step 208, a PPG signal for from the subject for analysis of the heart activity of the subject; and determining, step 210, a synthetic ECG signal of the subject based on the acquired PPG signal and the subject-specific model.

Using the model, the ECG signal may be estimated based only on the PPG signal. Thus, once the model is deployed, a synthetic ECG signal may be generated while the subject only wears a PPG sensor.

The acquiring of the PPG signal and determining of the synthetic ECG signal may be performed by the device comprising the PPG sensor. The device may thus also comprise the processor that receives the model. However, as an alternative, the model may be deployed on a processor which may be arranged in a separate physical unit from the PPG sensor, such as a mobile phone or a computer unit of the subject. Thus, acquiring of the PPG signal may comprise receiving the PPG signal from the PPG sensor by the processor, which then determines the synthetic ECG signal of the subject.

Once the synthetic ECG signal has been generated, the synthetic ECG signal may be further analyzed for determining features characterizing heart activity of the subject. For instance, the synthetic ECG signal may be analyzed in order to determine an instantaneous heart rate and/or heart rate variability of the subject.

Analysis of the synthetic ECG signal may comprise extracting R-peaks in the synthetic ECG signal. Each R-peak may thus indicate a point in time of a heart beat. A time interval between adjacent R-peaks may further be determined and may be used for determining instantaneous heart rate. Further, differences in R-R time intervals may be used for determining heart rate variability.

It should be realized that other features in the synthetic ECG signals may be used as indications on a heart beat for determining heart rate and/or heart rate variability. Also, other metrics relating to heart activity may be determined based on the synthetic ECG signal.

Figure 3:
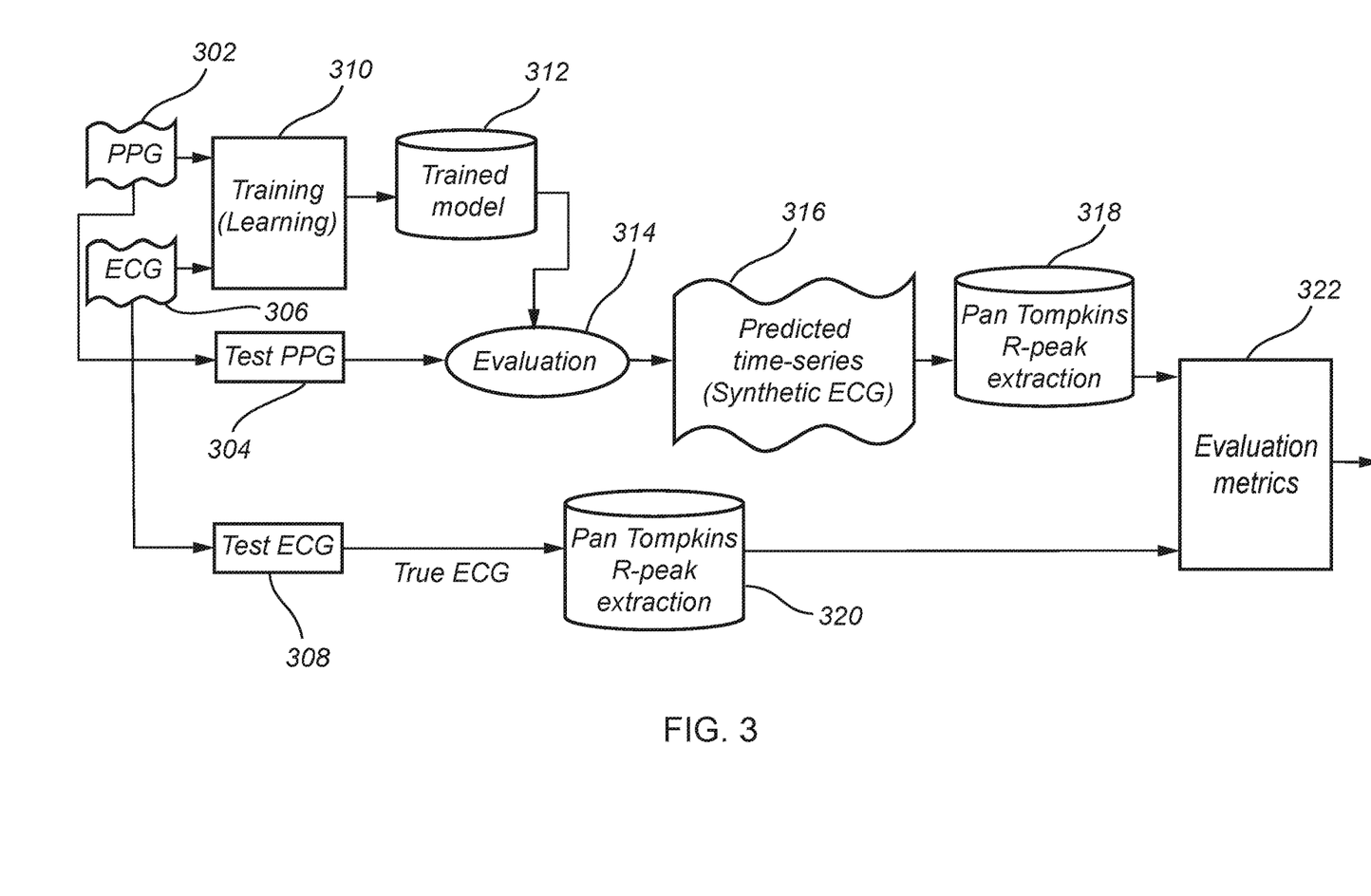
FIG. 3 is a flow chart illustrating training and evaluating of a machine-learned model according to an embodiment.

Referring now to FIG. 3, as a complement to the above description, an overview of training and verifying a machine-learned model is described.

A PPG signal is acquired, step 302. The PPG signal may be pre-processed, e.g. to remove high frequency noise component (outside heart rate frequencies) and DC drifts from the signal of interest.

The PPG signal may thus comprise a signal which is continuous in time (samples are equally spaced). The PPG signal may be divided into time periods, which may also be called windows or frames. Each window may be 2 seconds long, but it should be realized that other lengths of the periods may be used. The windows may be arranged in sequence or may be partially overlapping. For instance, a 1 second sliding window may be used, i.e. there may be a 1 second overlap between two sequential windows of the PPG signal.

The PPG signal may be formed into training data and test data, step 304. The training data may be used for training the neural network, whereas the test data may be used for testing the model to verify whether the model is successful in predicting the ECG signal from the PPG signal.

Further, an ECG signal may be acquired, step 306, to provide a ground truth. Further, the ECG signal may also be divided into windows, but in contrast to the windows of the PPG signal, the ECG signal may be divided into shorter time windows to ensure that heart beat information in a window of the ECG signal is observed in the corresponding PPG signal window (as the PPG signal is delayed in relation the ECG signal due to the PTT). The ECG signal may also be formed into training data provided to the neural network and test data, step 308.

Then, the training data part of the PPG signal and the ECG signal may be transferred to a DNN for forming the machine-learned model. The training data may associate PPG signal windows with ECG signal for corresponding windows. The ECG signal may thus provide a label of the ECG signal for each PPG signal window. The DNN may apply a deep learning algorithm, step 310, on the training data to determine relations between PPG signal and ECG signal.

Thus, a trained model is generated, step 312. The trained model may provide parameters for predicting a time series signal forming a synthetic ECG signal from new PPG signals.

The trained model may generate a time-series of a synthetic ECG signal which is shorter than the time-series of the PPG signal. For instance, based on a two-seconds long PPG signal, a one-second long synthetic ECG signal may be generated. With a one second sliding window of the PPG signal, a continuous synthetic ECG signal may be generated.

Having a one-second long window of the ECG signal may be suitable in relation to a typical heart rate, as within a one-second window at least one ECG peak should be present if the heart rate is 60 beats per minute.

Then, the test data of PPG signals and the parameters of the model are provided for evaluation, step 314, of the machine-learned model. In the evaluation, a predicted time-series is generated, step 316, using the machine-learned model on the PPG signals of the test data. The predicted time-series thus forms a synthetic ECG signal.

Then, R-peak extraction is performed, step 318, based on the synthetic ECG signal. The R-peak extraction may be based on Pan Tompkins's algorithm. Thus, extracted R-peaks may be provided for enabling verification of the machine-learned model.

Further, R-peak extraction of the test data of the ECG signal may also be performed, step 320, so as to enable the synthetic ECG signal to be verified against test ECG signals. The R-peak extraction from the test data of the ECG signal may also be based on Pan Tompkins's algorithm The extracted R-peaks from the synthetic ECG signal and the test ECG signal may thus be provided for determining an evaluation metric, step 322. The evaluation metric may define whether the machine-learned model adequately generates synthetic ECG signals and may thus be provided for controlling whether further training of the machine-learned model is to be performed or whether the machine-learned model may be deployed.

The machine-learned model may be periodically updated in order to ensure that the machine-learned model continues to reliably predict synthetic ECG signals from PPG signals of the subject. The updating of the machine-learned model may for instance adapt the machine-learned model to changing physiological factors of the subject.

The updating may e.g. be performed on a yearly basis.

The updating of the machine-learned model may comprise acquiring PPG signals and ECG signals providing ground truth. The PPG signals may first be used as test data to evaluate the existing machine-learned model based on the acquired PPG signals. The predicted ECG signals may be verified against the ground truth provided by the ECG signals based on comparison of extracted R-peaks as described above to determine whether the model reliably predicts ECG signals. If not, a new training period may be commenced, wherein PPG signals are acquired to form training data, step 302, and ECG signals are acquired to provide ground truth, step 306. Then, the new training data may be transferred to the DNN for generating the machine learned model, steps 310, 312. The generation of the machine-learned model may start in the existing model to improve the model or may be generated from scratch using only the new training data.

Figure 4:
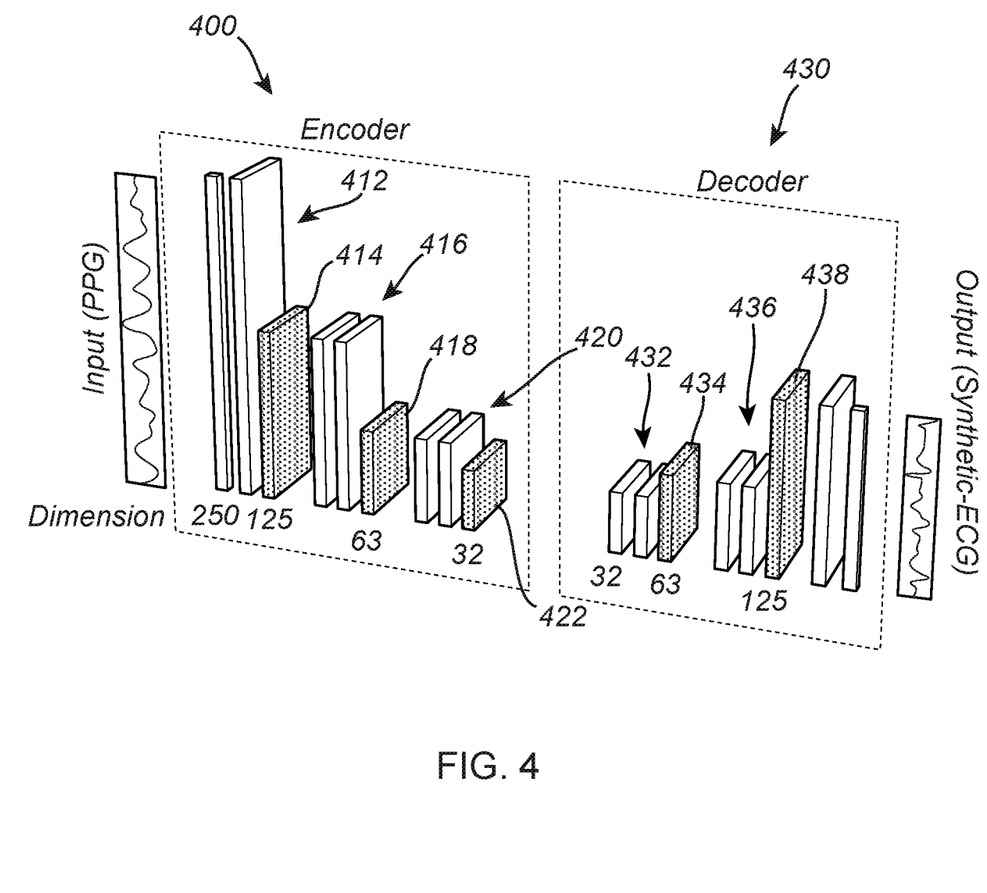
FIG. 4 is a schematic view of a stack of neural network layers used in generating the model.

Referring now to FIG. 4, an embodiment of the deep neural network (DNN) used for generating the model will be described in further detail.

A DNN may be configured to provide machine learning, wherein the neural network automatically discovers representations needed for feature detection or classification from raw data, so that manual feature engineering may not be needed and the neural network is able to both learn features and then use the features to perform a specific task.

A DNN may include multi-layer perceptrons (MLP), convolutional neural networks (CNN), and/or Recurrent Neural Networks (RNN). In the present embodiment, an encoder-decoder translation mechanism is used for translating time-series data, PPG signals to synthetic ECG signals.

In an embodiment, a deep convolution-deconvolution network interleaved with pooling and unpooling layers, respectively, is used. It has been found that such a stack of layers in the DNN is particularly efficient in forming a reliable model for converting PPG signals to synthetic ECG signals. However, it should be realized that other combination of layers may be used to also form a satisfactory model.

Convolutional layers may connect multiple input activations within a filter window to a single activation. In contrast, deconvolutional layers may associate a single input activation with multiple outputs. The deconvolutional layer may thus output an enlarged and dense activation map. A hierarchical structure of deconvolutional layers may be used to capture different levels of shape details.

In FIG. 4, a designed architecture according to an embodiment of the DNN for converting PPG signals to synthetic ECG signals is illustrated. The DNN 400 comprises an encoder stage 410 and a decoder stage 430.

The encoder stage 410 may comprise three stacked CNN layers 412, 416, 420 interleaved with pooling layers 414, 418, 422.

The decoder stage 430 may comprise two deconvolutional neural network (DCNN) layers 432, 436 interleaved with two unpooling layers 434, 438.

Each convolution operation in both the encoder and decoder stages 410, 430 may comprise one-dimensional CNN/DCNN operation with Scaled Exponential Linear Unit (SELU) activation, using 32 filters each of size 40 (max-pooling with size 2) and dropout rate of 0.1. This may ensure generalization thereby preventing the model from overfitting to a given set of trained data samples.

The DNN 400 has been used to train a machine-learned model to use two seconds of PPG signal (250 samples, using a sampling frequency of 125 Hz) at the encoder stage to predict one second (125 samples) of a synthetic ECG signal at the decoder stage.

Since the encoder stage 410 utilizes down-sampling to reduce dimensionality to enable the model to learn higher-order features of the data, there may be a need to upsample, or unpool, in the decoder stage 430. In an embodiment, the number of layers in the encoder and decoder stages 410, 430 were selected such that the 250 sample input could be reduced to a 125 sample output.

Additionally, there is a trade-off between models overfitting when having a complex structure which prevents generalization resulting in poor test scores and no real world efficacy. The two-layer structure illustrated in FIG. 4 has been evaluated to confirm that it is sufficiently complex for the model to learn a relationship between PPG and ECG signals, but not too complex that it overfits.

The DNN algorithm discussed above was evaluated on the IEEE Signal Processing Cup (SPC) 2015 database, see Zhilin Zhang, Zhouyue Pi, Benyuan Liu, "TROIKA: A General Framework for Heart Rate Monitoring Using Wrist-Type Photoplethysmographic Signals During Intensive Physical Exercise", IEEE Transaction on Biomedical Engineering, vol. 62, no. 2, pages 522-531, February 2015. The IEEE SPC 2015 database comprises PPG signals of 5-minute duration, from 20 healthy subjects, age ranging 18 to 58.

The DNN algorithm was evaluated on subjects 1-12, involving walking or running on a treadmill with the following speeds in order: 1-2 km/h for 0.5 min, 6-8 km/h for 1 min, 12-15 km/h for 1 min, 6-8 km/h for 1 min, 12-15 km/h for 1 min, and 1-2 km/h for 0.5 min. The subjects used their hand (with wristband) to pull clothes, wipe sweat on forehead, and push buttons on the treadmill.

The evaluation was made based on predicted R-peaks in the synthetic ECG signal in relation to actual ECG R-peaks.

Evaluation metrics were based on the following definitions:

FP=False Positive—occurs if the predicted R peak from the synthetic ECG signal does not correspond to an actual ECG peak.

FN=False Negative—occurs if there is no predicted R peak from the synthetic ECG signal for an actual ECG peak, and hence, if no peak is present in a one second window of the synthetic ECG signal, a peak of a previous window will be used in determining heart rate and/or heart rate variability, which results in a previous predicted peak being used for duplicate windows.

TP=True Positive—occurs when absolute distance between the two peaks is less than a threshold.

True R=number of actual ECG peaks

Based on these definitions, the following metrics were used:

$$Accuracy = \frac{TP}{\#True\ R}$$
$$Sensitivity = \frac{TP}{TP+FN}$$
$$Precision = \frac{TP}{TP+FP}$$

In the evaluation on the 12 subjects, a mean accuracy of 92.8%, a mean sensitivity of 93.7% and a mean precision of 94.3% were achieved, indicating that the model may be efficient in generating a synthetic ECG signal which reliably predicts R peaks.

Figure 5:
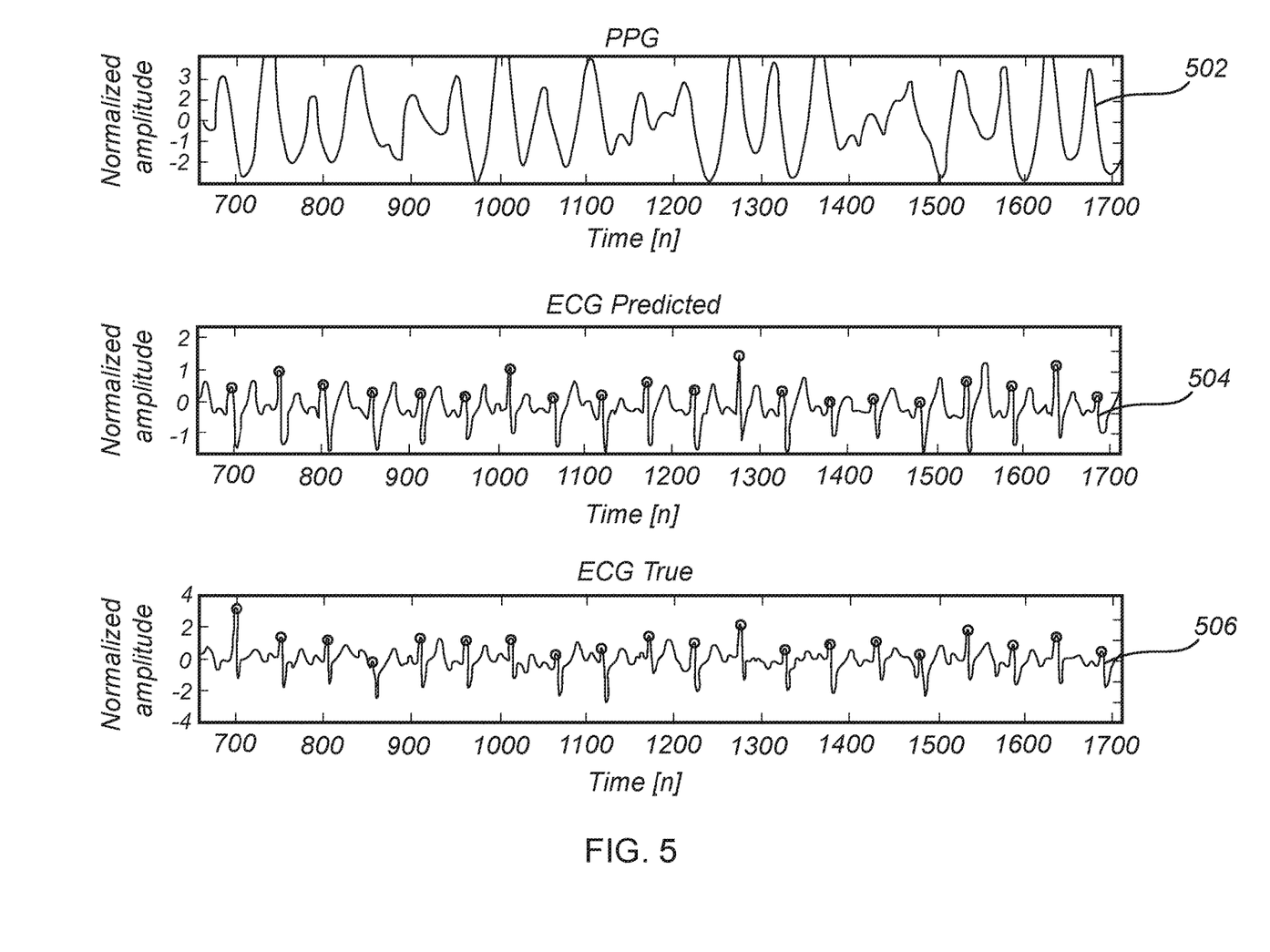
FIG. 5 is a graph illustrating a PPG signal, a synthetic ECG signal predicted based on the PPG signal, and a corresponding true ECG signal.

Referring now to FIG. 5, an illustrative example is presented, wherein a PPG signal 502, a synthetic ECG signal 504 predicted based on the PPG signal 502 using the determined machine-learned model, and a corresponding true ECG signal 506 are shown.

The R-peaks in the synthetic ECG signal 504 and the true ECG signals 506 are marked by circles, illustrating a high correspondence between predicted R-peaks and true R-peaks.

Figure 6:
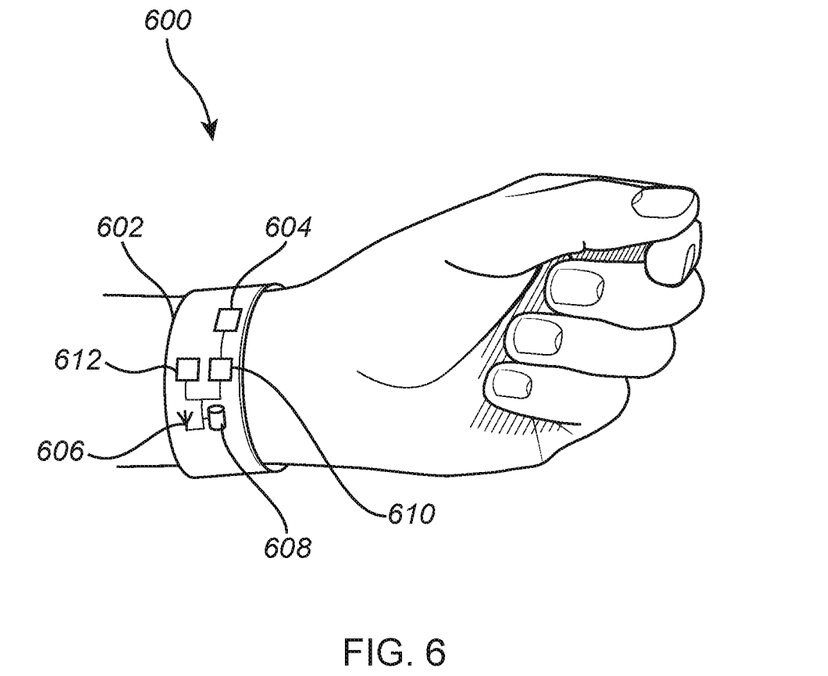
FIG. 6 is a schematic view of a device for heart rate estimation from a PPG signal according to an embodiment.

Referring now to FIG. 6, a device 600 will be described. The device 600 may be used for acquiring at least the PPG signal for subject-specific training data and may receive a machine-learned model based on the training data such that the device 600 may, after a training period, be used for predicting ECG signals based on acquired PPG signals.

The device 600 may comprise a carrier 602, which may have a shape adapted for being worn by a subject. For instance, the carrier 602 may be in the form of a wristband, which may be worn on a wrist of the subject.

The carrier 602 may be configured to carry components of the device 600 such that the components are provided to be worn by the subject.

The device 600 may further comprise a PPG sensor 604. The PPG sensor 604 may comprise a light source for emitting light and a light sensor for detecting an intensity of light. The PPG sensor 604 may be mounted in or on the carrier 602 so as to enable the light source to emit light towards a skin surface of the subject so that light will interact with blood flow in the subject. The light sensor is arranged to detect light having interacted with the blood flow. The detected light will thus be modulated by the heart pulse of the subject, such that the ECG signal may be predicted using the machine-learned model.

The PPG sensor 604 may be arranged so that reflected light is detected by the light sensor. However, it should be realized that the PPG sensor 604 may alternatively be arranged in the carrier 602 so that transmitted light is detected, e.g. by arranging the light source and the light sensor on opposite sides of a body part of the subject. Using a transmissive mode may be particularly feasible if the carrier 602 is to be worn around a relatively thin body part, such as a fingertip or an earlobe.

The light source of the PPG sensor 604 may be configured to emit green light, which may produce large intensity variations based on modulation by the heart pulse of the subject. However, it should be realized that other wavelengths of light may be used, such as infrared light.

The device 600 may further comprise a communication unit 606, which may be configured to communicate with a neural network for transferring subject-specific training data to the neural network. The communication unit 606 may be configured for wired or wireless communication. For instance, the communication unit 606 may be configured to transfer training data to a specific external unit to which a connection is set up. Then, the specific external unit may forward the training data to the neural network, e.g. over a computer and/or telecommunication network. The communication unit 606 may for instance be paired with the specific external unit for wireless communication therewith or the device 600 may be docked with the specific external unit for providing training data via a wired connection.

The communication unit 606 may further be configured to receive the machine-learned model back from the neural network to deploy the machine-learned model in the device 600.

The device 600 may thus store the machine-learned model in a memory 608.

The device 600 may further comprise a processor 610, which is configured to access the machine-learned model. The processor 610 may further be configured to receive PPG signals from the PPG sensor 604. The processor may then process the PPG signals based on the machine-learned model and may determine a predicted ECG signal.

The device 600 may further comprise a display and the processor 610 may be configured to output estimated heart rates to the display so as to allow the subject to be informed of current heart rates.

The device 600 may further comprise a receiver 612, which may be configured to be connected to an ECG sensor for acquiring an ECG signal from the subject, which may provide a ground truth for subject-specific training.

The ECG sensor may be arranged in a separate physical unit and need not be part of the device 600.

The receiver 612 may thus receive the ECG signal via the communication unit 606, which may be configured to communicate with the ECG sensor, e.g. over a wireless communication. The receiver 612 may be implemented as a process within the device 600, e.g. executed by the processor 608, wherein the ECG signal data may e.g. be registered into the memory 608 for enabling the data to be combined or associated with PPG signals.

The device 600 may further be configured to combine PPG signals and ECG signals into common package(s) for transferring the subject-specific training data to the neural network.

According to an alternative, the device 600 need not comprise the receiver 612. Rather, the ECG sensor may be configured to separately transfer ECG signals to the neural network, which may then associate the ECG signals with the PPG signals.

The processor 610 may be implemented as a processing unit, such as a central processing unit (CPU), which may execute the instructions of one or more computer programs in order to implement functionality of the device 600.

The processor 610 may alternatively be implemented as firmware arranged e.g. in an embedded system, or as a specifically designed processing unit, such as an Application-Specific Integrated Circuit (ASIC) or a Field-Programmable Gate Array (FPGA), which may be configured to implement functionality of the device 600.

In the above the inventive concept has mainly been described with reference to a limited number of examples. However, as is readily appreciated by a person skilled in the art, other examples than the ones disclosed above are equally possible within the scope of the inventive concept, as defined by the appended claims.

For instance, verification of the synthetic ECG signal has been mainly described in relation to using Pan Tompkins's algorithm, which has been utilized in verification of results of the developed machine-learned model. It should be realized that other algorithms known to the person skilled in the art may be used and that Pan Tompkins's algorithm itself has limitations relating to analyzing ECG data acquired during motion.

What is claimed is:

1. A method of generating a model for generating a synthetic electrocardiography, ECG, signal, said method comprising:
    receiving subject-specific training data for machine learning, said training data comprising a photoplethysmography, PPG, signal acquired from a subject and an ECG signal acquired from the subject, wherein the ECG signal provides a ground truth of the subject for associating the ECG signal with the PPG signal;
    using associated pairs of a time-series of the PPG signal and a corresponding time-series of the ECG signal as input to a deep neural network, DNN; and
    determining, through the DNN, a subject-specific model relating the PPG signal of the subject to the ECG signal of the subject for converting the PPG signal to a synthetic ECG signal using the subject-specific model,
    wherein the subject-specific model is configured to convert a first time-series of the PPG signal to a second time-series of the synthetic ECG signal, wherein the second time-series is shorter than the first time-series.

2. The method according to claim 1, further comprising associating the determined subject-specific model with the subject.

3. The method according to claim 1, wherein the time-series of the PPG signal and the corresponding time-series of the ECG signal in an associated pair represent slightly different points in time to take pulse transit time into account.

4. The method according to claim 1, wherein the DNN comprises one or more convolutional neural network, CNN, layers, followed by one or more deconvolutional neural network, DCNN, layers.

5. The method according to claim 1, wherein the received subject-specific training data comprises a set of PPG signals and a set of ECG signals, each set including signals acquired in relation to different activities of the subject.

6. The method according to claim 1, wherein said training data further comprises abnormality data corresponding to abnormalities of heart functioning acquired from other subjects, said abnormality data comprising a PPG signal and an associated ECG signal.

7. A non-transitory computer-readable medium having stored thereon computer-readable instructions such that when executed on a processing unit the computer-readable instructions will cause the processing unit to perform a method of generating a model for generating a synthetic electrocardiography, ECG, signal, said method comprising:
    receiving subject-specific training data for machine learning, said training data comprising a photoplethysmography, PPG, signal acquired from a subject and an ECG signal acquired from the subject, wherein the ECG signal provides a ground truth of the subject for associating the ECG signal with the PPG signal;
    using associated pairs of a time-series of the PPG signal and a corresponding time-series of the ECG signal as input to a deep neural network, DNN; and
    determining, through the DNN, a subject-specific model relating the PPG signal of the subject to the ECG signal of the subject for converting the PPG signal to a synthetic ECG signal using the subject-specific model,
    wherein the subject-specific model is configured to convert a first time-series of the PPG signal to a second time-series of the synthetic ECG signal, wherein the second time-series is shorter than the first time-series.

8. A method for analysis of heart activity of a subject based on a photoplethysmography, PPG, signal from the subject, said method comprising:
    acquiring subject-specific training data for machine learning, said training data comprising a PPG signal acquired from the subject and an electrocardiography, ECG, signal acquired from the subject, wherein the ECG signal provides a ground truth of the subject for associating the ECG signal with the PPG signal;
    transferring the subject-specific training data to a deep neural network, DNN; receiving a subject-specific machine-learned model from the DNN, wherein the model defines a relation of a time-series of the PPG signal of the subject to a corresponding time-series of the ECG signal of the subject;
    acquiring a PPG signal from the subject for analysis of the heart activity of the subject; and
    determining a synthetic ECG signal of the subject based on subject-specific model and the acquired PPG signal for analysis of the heart activity of the subject,
    wherein the subject-specific model is configured to convert a first time-series of the PPG signal to a second time-series of the synthetic ECG signal, wherein the second time-series is shorter than the first time-series.

9. The method according to claim 8, further comprising extracting R-peaks based on the synthetic ECG signal.

10. The method according to claim 8, wherein the training data is acquired during an initial training period for generation of the machine-learned model, and after the subject-specific machine-learned model has been generated, the
    determining of the synthetic ECG signal of the subject based on the PPG signal is enabled.

11. The method according to claim 10, further comprising updating the subject-specific machine-learned model after the subject-specific machine-learned model has been initially generated, said updating comprising during an updating training period:
    acquiring subject-specific updating training data for machine learning, said updating training data comprising a PPG signal from the subject and an ECG signal from the subject, wherein the ECG signal provides a ground truth of the subject for associating the ECG signal with the PPG signal;
    transferring the subject-specific updating training data to the DNN;
    receiving an updated subject-specific machine-learned model from the DNN, wherein the updated model defines a relation of a time-series of the PPG signal of the subject to a corresponding time-series of the ECG signal of the subject.

12. A system for analysis of heart activity of a subject based on a photoplethysmography, PPG, signal from the subject, said system comprising:
- a PPG sensor for acquiring a PPG signal from the subject,
- a communication unit, which is configured to communicate with a deep neural network, DNN, for machine learning, wherein the communication unit is configured to acquire from the PPG sensor subject-specific training data for machine learning, said training data comprising the PPG signal acquired from the subject; the communication unit being further configured to transfer the subject-specific training data to the DNN, which further receives an electrocardiography, ECG, signal acquired from the subject, wherein the ECG signal provides a ground truth of the subject for associating the ECG signal with the PPG signal, and the communication unit being further configured to receive a subject-specific machine-learned model from the DNN, wherein the model defines a relation of a time-series of the PPG signal of the subject to a corresponding time-series of the ECG signal of the subject; and
- a processor, which is configured to receive the subject-specific model from the communication unit and, after receiving the subject-specific model, receive the PPG signal from the PPG sensor for analysis of the heart activity of the subject,
- wherein the processor is configured to determine a synthetic ECG signal of the subject based on the received subject-specific model and the PPG signal for analysis of the heart activity of the subject,
- wherein the subject-specific model is configured to convert a first time-series of the PPG signal to a second time-series of the synthetic ECG signal, wherein the second time-series is shorter than the first time-series.

13. The system according to claim 12, further comprising a carrier, which is configured to be worn by the subject, wherein the PPG sensor, the communication unit and the processor are arranged in or on the carrier.

14. The system according to claim 12, wherein the processor is further configured to extract R-peaks based on the synthetic ECG signal.

15. The system according to claim 12, further comprising a memory for storing the subject-specific model.

16. The system according to claim 15, wherein the memory is configured to store a plurality of models for different subjects and the system is configured to activate a relevant subject-specific model.

17. The system according to claim 12, further comprising an ECG sensor for acquiring the ECG signal.

18. The system according to claim 12, wherein the PPG sensor is configured to detect the PPG signal from the subject by emitting green light towards a skin surface of the subject and detecting reflected light having interacted with blood flow of the subject.

* * * * *